US009115176B2

(12) United States Patent
Hocquaux et al.

(10) Patent No.: US 9,115,176 B2
(45) Date of Patent: Aug. 25, 2015

(54) COMPOUNDS, USE THEREOF IN COSMETIC AND COSMECEUTIC APPLICATIONS, AND COMPOSITIONS COMPRISING SAME

(75) Inventors: Michel Hocquaux, Paris (FR); Estelle Loing, Quebec (CA); Philippe Bedos, Donneville (FR)

(73) Assignee: Lucas Meyer Cosmetics Canada Inc. (CA)

( * ) Notice: Subject to any disclaimer, the term of this patent is extended or adjusted under 35 U.S.C. 154(b) by 956 days.

(21) Appl. No.: 12/452,368

(22) PCT Filed: Jun. 30, 2008

(86) PCT No.: PCT/CA2008/001226

§ 371 (c)(1), (2), (4) Date: Aug. 25, 2010

(87) PCT Pub. No.: WO2009/003283

PCT Pub. Date: Jan. 8, 2009

(65) Prior Publication Data

US 2010/0311667 A1 Dec. 9, 2010

Related U.S. Application Data

(60) Provisional application No. 60/947,144, filed on Jun. 29, 2007, provisional application No. 60/984,136, filed on Oct. 31, 2007.

(51) Int. Cl.

*C07K 5/11* (2006.01)
*A61K 8/64* (2006.01)
*A61Q 19/08* (2006.01)
*A61K 38/00* (2006.01)

(52) U.S. Cl.

CPC ................ *C07K 5/1019* (2013.01); *A61K 8/64* (2013.01); *A61Q 19/08* (2013.01); *A61K 38/00* (2013.01)

(58) Field of Classification Search

CPC ......... A61K 38/00; A61K 8/64; A61Q 19/08; C07K 5/1019

See application file for complete search history.

(56) References Cited

U.S. PATENT DOCUMENTS

| | | | | |
|---|---|---|---|---|
| 5,830,994 | A | 11/1998 | D'Hinterland et al. | |
| 6,558,422 | B1 | 5/2003 | Baker et al. | |
| 7,507,719 | B2 | 3/2009 | Pinel et al. | |
| 2007/0004633 | A1 * | 1/2007 | Pinel et al. | 514/17 |

FOREIGN PATENT DOCUMENTS

| | | | | | |
|---|---|---|---|---|---|
| WO | WO-95/08564 | A1 | 3/1995 | | |
| WO | 97/18235 | * | 5/1997 | | C07K 7/06 |
| WO | WO-97/18235 | | 5/1997 | | |
| WO | WO-2005009402 | A2 | 2/2005 | | |
| WO | WO-2005009456 | A2 | 2/2005 | | |

OTHER PUBLICATIONS

"International Application Serial No. PCT/CA2008/001226, International Search Report and Written Opinion", (Oct. 17, 2008), 15 pgs.

"International Application No. PCT/CA2008/001226, International Preliminary Report on Patentability issued Jan. 5, 2010", 8 pgs.

"U.S. Appl. No. 12/452,381, Non-Final Office Action mailed Jun. 28, 2012", 7 pgs.

"Australian Application Serial No. 2008271875, Examination Report mailed Sep. 14, 2012", 3 pgs.

"Chinese Application Serial No. 200880104710.1, Office Action mailed Dec. 19, 2011", (w/ English Translation), 10 pgs.

"International Application No. PCT/CA2008/001227, International Preliminary Report on Patentability mailed Jan. 14, 2010", 10 pgs.

"International Application Serial No. PCT/CA2008/001227, International Search Report and Written Opinion mailed Sep. 22, 2008", 16 pgs.

Remington: The Science and Practice of Pharmacy, 19th Edition, Mack Publishing Co., Easton, PA, Gennaro, A. R., Editor, (1995), 1399-1404.

"South Korean Application Serial No. 10-2010-7002248. Office Action mailed Jan. 19, 2012", (English Translation), 8 pgs.

Corbett, J. T., "The scopoletin assay for hydrogen peroxide—A review and a better method", *Journal of Biochemical and Biophysical Methods*, 18, (1989), 297-308.

De Méo, M., et al., "Genotoxic activity of potassium permanganate in acidic solutions", *Mutation Research*, 260, (1991), 295-306.

Emonet, N., et al., "Thiols and selenium: protective effect on human skin fibroblasts exposed to UVA radiation", *Journal of Photochemistry and Photobiology B: Biology*, 40, (1997), 84-90.

Halliwell, B., "Antioxidant Characterization—Methodology and Mechanism", *Biochemical Pharmacology*, 49(10), (1995), 1341-1348.

Kligman, L. H., et al., "Biochemical Changes in Hairless Mouse Skin Collagen After Chronic Exposure to Ultraviolet-A Radiation", *Photochemistry and Photobiology*, 54(2), (1991), 233-237.

Kligman, L. H, et al., "The Contributions of UVA and UVB to Connective Tissue Damage in Hairless Mice", *Journal of Investigative Dermatology*, 84(4), (1985), 272-276.

(Continued)

*Primary Examiner* — Suzanne Ziska

(74) *Attorney, Agent, or Firm* — Schwegman Lundberg & Woessner, P.A.

(57) ABSTRACT

A compound of the formula I: R-A-Gly-His-B (I) wherein: A and B are independently of each other a L-lysine residue, a D-lysine residue, or a L- or D-lysine residue in which the $NH_2$ group of the side chain comprises a modification, where-in said modification is (i) a replacement with a hydrogen, (ii) an acetylation, (iii) a benzoylation, or (iv) a palmitoylation; GIy is a glycine residue; His is a L- or D-histidine residue; R is $CH_3$—$(CH_2)_n$—CO—, wherein n=2, 3, 4, 5, 6, 7 or 8; R' is a group of formula (II): N(Z)(Z') (II) wherein: Z and Z' is hydrogen, a methyl group, an ethyl group, a phenyl group, an hexyl group, a decyl group or an hexadecyl group; or a racemate, an enantiomer or a diastereomer thereof, or mixtures thereof, or a salt thereof.

19 Claims, 4 Drawing Sheets

(56) References Cited

OTHER PUBLICATIONS

Matsueda, G. R., et al., "A *p*-Methylbenzhydrylamine Resin for Improved Solid-Phase Synthesis of Peptide Amides", *Peptides*, vol. 2, (1981), 45-50.

Pflaum, M., et al., "Visible light generates oxidative DNA base modifications in high excess of strand breaks in mammalian cells", Carcinogenesis, 15(2), (1994), 297-300.

Podda, M., et al., "Low molecular weight antioxidants and their role in skin ageing", *Clinical and Experimental Dermatology*, 26, (2001), 578-582.

Reed, L. J., "From lipoic acid to multi-enzyme complexes", *Protein Science*, 7, (1998), 220-224.

Rink, H., "Solid-Phase Synthesis of Protected Peptide Fragments Using a Trialkoxy-Diphenyl-Methylester Resin", *Tetrahedron Letters*, 28(33), (1987), 3787-3790.

Tyrrell, R. M., et al., "Correlation Between Endogenous Glutathione Content and Sensitivitiy of Cultured Human Skin Cells to Radiation at Defined Wavelengths in the Solar Ultraviolet Range", *Photochemistry and Photobiology*, 47(3), (1988), 405-412.

"Chinese Application No. 2008801047101, Second Office Action mailed Nov. 5, 2012", 3 pgs.

"Korean Application No. 10-2010-7002248, Final Rejection dated Nov. 20, 2012", 2 pgs.

"Chinese Application Serial No. 200880104710.1, Decision of Rejection mailed Apr. 2, 2013", 13 pgs.

"Japanese Application No. 2010-513593, Office Action issued Jun. 28, 2013", 5 pgs.

"European Application No. 08 78 3164, Supplementary European Search Report dated Mar. 24, 2014", 7 pgs.

"Korean Application No. 10-2010-7002248, Trial Decision dated Jun. 27, 2014", 1 pg.

Schoepe, S., et al., "Glucocorticoid therapy-induced skin atrophy", Experimental Dermatology 2006: 15: 406-420, (Mar. 15, 2006), 406-420.

* cited by examiner

Day 0

Day 28

| | *Mean evolution** (%) | | | |
|---|---|---|---|---|
| | ***SPt*** | ***SPa*** | ***SPq*** | ***SDev*** |
| ***Means at T28 days*** | *-3,0%* | *-4,6%* | *-4,7%* | *-0,1%* |
| ***Means at T56 days*** | *-4,4%* | *-5,3%* | *-5,1%* | *-0,1%* |

* : percentages calculated based on the averages of the raw values

| | *Mean evolution* (%)* |
|---|---|
| | **Average Roughness (mm)** |
| **Means at T28 days** | **-2,3%** |
| **Means at T56 days** | **-4,1%** |

* : percentages calculated based on the averages of the raw values

COMPOUNDS, USE THEREOF IN COSMETIC AND COSMECEUTIC APPLICATIONS, AND COMPOSITIONS COMPRISING SAME

CROSS REFERENCE TO RELATED APPLICATIONS

This application is a national stage application under 35 U.S.C. §371 of PCT/CA2008/001226, filed Jun. 30, 2008, and published as WO 2009/003283A1, on Jan. 8, 2009, which claims benefit of U.S. provisional application Ser. No. 60/947,144, filed on Jun. 29, 2007, and of U.S. provisional application Ser. No. 60/984,136, filed on Oct. 31, 2007. All documents above are incorporated herein in their entirety by reference.

FIELD OF THE INVENTION

The present invention generally relates to cosmetic, dermatological and pharmaceutical compositions and to food supplements. More specifically, the present invention relates to compounds, compositions and treatment/prevention methods for skin conditions, e.g., for preventing or treating signs of aging of the skin, such as wrinkles and fine lines, as well as the loss of skin firmness and elasticity.

BACKGROUND OF THE INVENTION

The epidermis and the dermis, separated by the basal membrane, constitute the cutaneous covering on the hypoderm. The epidermis is the most superficial layer of the skin and provides its resistance and impermeability.

Although different types of cells coexist in the epidermis, keratinocytes make up the majority of this layer and play a role in the resistance provided by the mucocutaneous barrier. The core activity of these cells is the synthesis of keratins, which represent close to 90% of all the protein in the epidermis.

The dermis, the internal layer of the skin, is conjunctive tissue composed of cells (essentially fibroblasts) dispersed in a complex medium called the extracellular matrix (ECM). This matrix consists of collagen and elastin fibres, glycoproteins (fibronectin and laminin) and proteoglycans. The extracellular matrix serves as a structure for the cells, allowing tissues and organs to cohere in pluricellular organisms.

Interactions between the cells of the epidermis and the fibres of the dermis play a significant role in controlling cellular behaviour, such as in healing, for example, but also provide stability to the dermo-epidermal junction (DEJ), which anchors the epidermis to the dermis and forms a protective barrier. The DEJ acts at several levels. First, it serves as a mechanical support, using the collagen IV network to solidly anchor the epidermis to the dermis. It also plays a biological role by establishing direct relationships with the basal cells of the epidermis. It further serves as a significant reservoir for growth factors. Finally, it supports keratinocytes during the healing process.

The DEJ consists of two laminae: (A) The basal lamina, to which epidermal cells adhere. The basal lamina is itself composed of two layers: the lamina lucida and the lamina densa. This is where is found type IV collagen, proteoglycans and glycoproteins, components that are organized in the anchoring filaments that create the laminae. Laminins are glycoproteins that allow the keratinocytes to adhere to the basal lamina. Many laminins are present in the basal lamina, among which the most common are laminin-5, laminin-6 and laminin-7, and laminin-1. Laminin-5 (also known as laminin 332), a multi-purpose matrix protein, is the most commonly found laminin in the skin's basal membrane. It is the most common adherence protein for cells in the epidermis. Laminin-5 serves a double purpose: it can induce a strong and strategic cellular adherence or, on the contrary, it can produce a weak, temporary adherence for cellular migration. This property is well illustrated in the skin, since, although laminin-5 anchors the epidermis, it also plays a role in the migration of keratinocytes during the healing process. Studies of skin healing in vivo have shown greater expression of pre-laminin-5 in the ECM of keratinocytes located in the wound's colonization zone, indicating that the absence of proteolytic maturation fosters cellular migration. Laminin-5 further plays a key role in cellular restructuring and scar formation.

(B) The reticular lamina: Also known as the sub-lamina densa, it is connected to the dermis and consists of a dense matrix formed in part of collagen VII, III and I filaments and basic substances. Collagen VII, synthesized mainly by keratinocytes, is the major component of the sub-lamina densa and represents an essential anchoring fibre. Connected to the laminin-5 or collagen IV of the lamina densa, the anchoring fibril protein collagen VII reaches down into the dermal matrix. Anchoring fibres form solid structures whose functional role is to tie the lamina densa to the papillary dermis, where they attach to dermal collagen fibres made of types I, III and V collagen. At its N-terminal extremity, each triple helix of collagen VII is flanked by a globular NC1 domain. Two of these chains link at their C-terminal ends to form a dimer. These dimers are short striated fibrils that combine laterally to form anchoring fibrils. The collagen VII interacts with the other components of the extracellular matrix through its NC1 domain, attaching to the laminin-5 and anchoring the basal membrane to the dermis where it connects to the other types of collagen (I and III). It would appear that some genetic and orphan diseases may be due to an absence of collagen VII. Any molecule found in either one of the basal lamina and/or the reticular lamina such as collagen, proteoglycans and glycoproteins including laminins is called herein a DEJ molecule.

Aging of the skin results from two processes: (1) an intrinsic process, corresponding to chronological aging, and (2) an extrinsic process resulting mainly from the deleterious effect of exposure to the sun and environmental pollution.

Upon aging, major changes within connective components of the dermis can be seen: collagen looses its regular and fascicular appearance, while ground substance increases, elastic material decreases and the fibroblast cell population becomes "at rest". Also, during the skin aging process, the DEJ progressively loses its ability to fulfill its mechanical function, resulting in a weakening of the epidermis-dermis interface. The resulting dermal aging is different according to individuals and is related to genetic background and exposition to multiple aggressions.

One of the objectives in cosmetological research is to control or prevent skin aging. Traditional approaches based on the supply of keratinocytes and the metabolism of fibroblasts are now known to be inadequate, particularly in light of recent data on the DEJ.

Therefore, this is a need to develop new approaches for the prevention and/or treatment of skin condition such as the aging of the skin.

SUMMARY OF THE INVENTION

More specifically, in accordance with the present invention, there is provided a compound of the formula I (SEQ ID NO: 5):

$$\text{R-A-Gly-His-B—R'} \qquad \text{(I)}$$

wherein: A and B are independently of each other a L-lysine residue, a D-lysine residue, or a L- or D-lysine residue in which the $NH_2$ group of the side chain comprises a modification, wherein said modification is (i) a replacement with a hydrogen, (ii) an acetylation, (iii) a benzoylation, or (iv) a palmitoylation; Gly is a glycine residue; His is a L- or D-histidine residue; R is an amino terminal modification of formula $CH_3$—$(CH_2)_n$—CO—, wherein n=2, 3, 4, 5, 6, 7 or 8; R' is a group of formula (II):

$$N(Z)(Z') \quad (II)$$

wherein: Z and Z' are independently of each other hydrogen, a methyl group, an ethyl group, a phenyl group, a hexyl group, a decyl group or a hexadecyl group; or a racemate, an enantiomer or a diastereomer thereof, or mixtures thereof, or a salt thereof.

In a specific embodiment of the compound of the present invention, n=4, 5 or 6. In another specific embodiment, Z and Z' are hydrogen. In another specific embodiment, A and B are independently of each other a L-lysine residue or a D-lysine residue. In another specific embodiment, the lysine and histidine residues are in L-configuration. In another specific embodiment, said compound is $CH_3$—$(CH_2)_4$—CO-Lys-Gly-His-Lys-$NH_2$ (SEQ ID NO:1) or $CH_3$—$(CH_2)_6$—CO-Lys-Gly-His-Lys-$NH_2$ (SEQ ID NO:2). In another specific embodiment, said compound is $CH_3$—$(CH_2)_4$—CO-Lys-Gly-His-Lys-$NH_2$ (SEQ ID NO:1). In SEQ ID NOs: 1 to 4, -Lys-$NH_2$ denotes an amidation of the carboxylic group of the lysine residue (i.e., —$CONH_2$)

In accordance with another aspect of the present invention, there is provided a composition comprising an effective amount of the compound of the present invention, and a topically, cosmetically or pharmaceutically acceptable excipient or carrier.

In another aspect, the present invention provides a composition for preventing, reducing, delaying or treating a skin condition in a subject, said composition comprising the compound of the present invention, and a topically, cosmetically or pharmaceutically acceptable excipient or carrier.

In another aspect, the present invention provides a composition for inducing or increasing the production of at least one dermo-epidermal junction (DEJ) molecule in a biological system, said composition comprising the compound of the present invention, and a topically, cosmetically or pharmaceutically acceptable excipient or carrier.

In another aspect, the present invention provides the compound of the present invention for preventing, reducing, delaying or treating a skin condition in a subject.

In another aspect, the present invention provides the compound of the present invention for inducing or increasing the production of at least one dermo-epidermal junction (DEJ) molecule in a biological system.

In a specific embodiment of the composition, said effective amount is between about $10^{-8}$ M to about $10^{-2}$ M. In another specific embodiment, said effective amount is between about $10^{-6}$ M to about $10^{-5}$ M. In another specific embodiment, said composition is a topical composition. In another specific embodiment, said composition is an aqueous solution, a cream, a water-in-oil emulsion, a oil-in-water emulsion, a gel, a spray, an ointment, a lotion, or a paste. In another specific embodiment, the composition further comprises at least one additional active agent.

In accordance with another aspect of the present invention, there is provided a use of the compound of the present invention, or the composition of the present invention, for preventing, reducing, delaying or treating a skin condition.

In a specific embodiment, the use of the compound or the composition of the present invention is for the preparation of a medicament for preventing, reducing, delaying or treating a skin condition.

In another specific embodiment, said skin condition is an aging-related skin condition. In another specific embodiment, said aging-related skin condition is the appearance or presence of (a) wrinkles, (b) fine lines or (c) both (a) and (b), on the skin. In another specific embodiment, said skin condition is a skin injury. In another specific embodiment, said skin injury is associated with surgical treatment, dermabrasion, laser treatment or peeling.

In another specific embodiment, the use of the compound or the composition is for inducing or increasing the production of at least one dermo-epidermal junction (DEJ) molecule in a biological system.

In another specific embodiment, said at least one DEJ molecule is (a) laminin-5, (b) collagen VII, or (c) both (a) and (b). In another specific embodiment, said biological system is a cell, a tissue or an organ. In another specific embodiment, said cell is a skin cell. In another specific embodiment, said organ is skin.

In accordance with another aspect of the present invention, there is provided a method of preventing, reducing, delaying or treating a skin condition in a subject, said method comprising administering an effective amount of the compound of the present invention, or the composition of the present invention, to said subject. In a specific embodiment of the method, said skin condition is an aging-related skin condition. In another specific embodiment, said aging-related skin condition is the appearance or presence of (a) wrinkles, (b) fine lines or (c) both (a) and (b), on the skin. In another specific embodiment, said skin condition is a skin injury. In another specific embodiment, said skin injury is associated with surgical treatment, dermabrasion, laser treatment or peeling. In another specific embodiment, the administration is topical. In another specific embodiment, said effective amount is between about $10^{-8}$ M to about $10^{-2}$M of said compound. In another specific embodiment, said effective amount is between about $10^{-6}$M to about $10^{-5}$M of said compound.

In accordance with another aspect of the present invention, there is provided a method for inducing or increasing the production of at least one dermo-epidermal junction (DEJ) molecule in a biological system, said method comprising contacting said biological system with the compound of the present invention, or the composition of the present invention. In a specific embodiment of the method, said at least one DEJ molecule is (a) laminin-5, (b) collagen VII, or (c) both (a) and (b). In another specific embodiment, said biological system is a cell, a tissue or an organ. In another specific embodiment, said cell is a skin cell. In another specific embodiment, said organ is skin.

In accordance with another aspect of the present invention, there is provided a kit or package comprising the compound of the present invention, or the composition of the present invention, together with instructions for preventing, reducing, delaying or treating a skin condition in a subject.

In accordance with another aspect of the present invention, there is provided a kit or package comprising the compound of the present invention, or the composition of the present invention, and a container.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
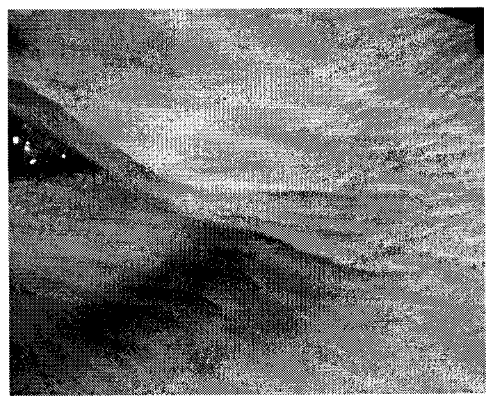
FIG. 1 is a photograph of the cow's feet of a volunteer at day 0 and day 28 after application of a composition comprising peptide I.

The applicant has found that a family of compounds, more particularly compounds of the formula I below, are useful for treating a skin condition, e.g. for preventing, delaying, reducing or treating the effects of aging on skin.

Accordingly, the present invention provides a compound of the following formula (I):

A compound of the formula I (SEQ ID NO: 5):

R-A-Gly-His-B—R' (I)

wherein:

A and B are independently of each other a L-lysine residue, a D-lysine residue, or a L- or D-lysine residue in which the $NH_2$ group of the side chain comprises a modification, wherein said modification is (i) a deamination (e.g., a replacement with a hydrogen), (ii) an acetylation, (iii) a benzoylation, or (iv) a palmitoylation;

Gly is a glycine residue;

His is a L- or D-histidine residue;

R is an amino terminal modification of formula $CH_3$—$(CH_2)_n$—CO—, wherein n=2, 3, 4, 5, 6, 7 or 8;

R' is a group of formula (II):

N(Z)(Z') (II)

wherein:

Z and Z' are independently of each other hydrogen, a methyl group, an ethyl group, a phenyl group, an hexyl group, a decyl group or an hexadecyl group;

or a racemate, an enantiomer or a diastereomer thereof, or mixtures thereof, or a salt thereof.

In a specific embodiment, the above-mentioned modifications of lysine residues are protecting groups for the amine functions of the lysine(s) lateral groups/side chains.

In specific embodiments, the amino terminal modification R provides a useful hydrophile/lipophile balance that favors skin penetration.

The compounds of formula (I) may have one or more asymmetrical carbon atoms in enantiomeric or diastereoisomeric form. Accordingly, the present invention provides enantiomers and diastereoisomers and their mixtures, including racemic mixtures, of the compounds of formula (I).

In an embodiment, the above-mentioned compound is $CH_3$—$(CH_2)_4$—CO-Lys-Gly-His-Lys-$NH_2$ (SEQ ID NO:1) or $CH_3$—$(CH_2)_6$—CO-Lys-Gly-His-Lys-$NH_2$ (SEQ ID NO:2). In a further embodiment, the above-mentioned compound is $CH_3$—$(CH_2)_4$—CO-Lys-Gly-His-Lys-$NH_2$ (SEQ ID NO:1).

The amino acids in the compound of the present invention may be present in their natural L-configuration, unnatural D-configuration, or as a racemic mixture (DL).

In a specific embodiment, the lysine and histidine residues of the compound are in L-configuration.

The compound of formula I of the present invention may be effectively obtained through classical chemical synthesis or by enzymatic synthesis through processes known to persons skilled in the art.

In accordance with the invention, a compound of the general formula (I) can be prepared following chemical synthesis processes in solution or on a solid support, e.g., synthesis on a support with resin. Among the resins that lend themselves to this use are Rink resin (or 4-(2',4'-dimethoxyphenyl-Fmoc-aminomethyl)-phenoxy resin) (H. Rink, Tetrahedron Let., 1987, 28, 3787) and MBHA resin (or 4-methyl-benzhydrylamine resin) (G. R. Matsueda et al., Peptides, 1981, 2, 45).

The initial products obtained are usually protected amino acids. The protective groups can be an acetyl (Ac) group or a 9-fluorenyl-methoxycarbonyl (Fmoc) group on the primary amino function, a tert-butyloxycarbonyl (Boc) group, a Trityl (Trt) group, and a 2,2,5,7,8-pentamethylchromane-6-sulfonyl (Pmc) group on lateral chain functions. Techniques and methods for washing, coupling and deprotecting amino acids/peptides are well known in the art. The peptide thus obtained may be analyzed using techniques well known in the art, e.g., High Performance Liquid Chromatography (HPLC) and mass spectroscopy.

The compound of the present invention may be modified using methods well known in the art, e.g., to increase its stability and/or to facilitate its uptake/absorption and/or to improve any other desirable characteristic or property of the compound that is known to one of skill in art. For example, the compound can be cyclized, charges on the compound may be neutralized, and the compound may be linked to other chemical moieties.

The above-mentioned compound may take the form of a salt prepared from any physiologically acceptable acid, organic or inorganic. In an embodiment, the above-mentioned salt is a salt that stabilizes the compound and is tolerated by the skin. In an embodiment, the above-mentioned salt is an acetate salt.

In another aspect, the present invention provides a composition (e.g., a cosmetic, dermatological or pharmaceutical composition), or a food supplement, comprising a compound of formula (I), or a salt thereof.

The present invention encompasses methods administering the compound in an effective amount to provide a desired result. When the compound of the present invention is used topically for instance, the compound of formula (I) is present in a concentration between about $10^{-8}$M to about $10^{-2}$M in the composition of the present invention. In a further embodiment, the compound of formula (I) may be present in a concentration between about $10^{-6}$M to about $10^{-5}$M in the composition of the present invention. In another embodiment, the compound of formula (I) is present in a concentration between about 0.5 mg/kg to about 50 mg/kg (i.e. 0.5 to 50 PPM or $0.88\times10^{-6}$M to $0.88\times10^{-4}$M) in the composition of the present invention.

The compound of formula (I) of the present invention may be formulated in a topically applicable cosmetic composition (e.g., a topical formulation). Non-limitative examples of such topically applicable compositions include skin care cream, cleansing cream, ointment, skin care lotion, skin care gel, skin care foam, sun care composition, make-up removal cream, make-up removal lotion, foundation cream, liquid foundation, bath and shower preparation, deodorant composition, antiperspirant composition, shaving products composition, after-shave gel or lotion, beauty aids composition, depilatory cream, soap composition, hand cleaner composition, cleansing bar, baby care, hair care, shampoo, setting lotion, treatment lotion, hair cream, hair gel, coloring composition, restructuring composition, permanent composition, anti-hair loss composition, or any other composition which is adapted for the use in a topical cosmetic regimen.

Creams, as is well known in the arts of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other cosmeceutically acceptable chemicals to buffer, stabilize or preserve the solute. Common examples of solvents used in preparing solutions are ethanol, water, propylene glycol or any other cosmeceutically acceptable vehicles.

Gels are semisolid, suspension-type systems. Single-phase gels contain organic macromolecules distributed substantially uniformly throughout the carrier liquid, which is typically aqueous, but also, preferably contain an alcohol, and, optionally, an oil. "Organic macromolecules," i.e., gelling agents, are crosslinked acrylic acid polymers such as the "carbomer" family of polymers, e.g., carboxypolyalkylenes that may be obtained commercially under Carbopol™. Other examples are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399 1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and, in the present context, encapsulate one or more components of the anti-aging formulations. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin™ (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the present formulations. Like liposomes and micelles, microspheres essentially encapsulate one or more components of the present formulations. They are generally although not necessarily formed from lipids, preferably charged lipids such as phospholipids. Preparation of lipidic microspheres is well known in the art and described in the pertinent texts and literature.

In an embodiment, the composition of the present invention further comprises at least one additional active ingredient/agent. In a further embodiment, the above-mentioned at least one additional active ingredient modulate(s) at least one of cell differentiation, cell metabolic activity, cell structure, cell proliferation, extracellular processes and pigmentation.

The composition of the present invention may further comprise at least one of an agent that modulates cell differentiation or proliferation, an anesthesic agent, anti-acne agent, anti-aging agent, antibacterial agent, anticellulite agent, antifungal agent, anti-inflammatory agent, anti-irritant agent, antioxidant agent, antiparasitic agent, antipollution agent, antipruritic agent, anti-rosacea agent, anti-seborrhea agent, anti-stress agent, anti-telangiectasia agent, antiviral agent, anti-wrinkle agent, baby care agent, bath and body agent, calming agent, cleansing agent, collagen synthesis agent, elastase inhibitory agent, exfoliant agent, facial peeling agent, firming agent, foot care agent, free radical scavenging agent, immune function modulator agent, keratolytic agent, lift agent, make-up remover agent, melanogenesis stimulator agent, hair care agent, matrix metalloproteinase inhibitory agent, moisturizing agent, oil absorbent agent, osmoregulator agent, anti-photoaging agent, protecting agent, rejuvenating agent, regenerating agent, restructuring agent, sensitive skin agent, shaving product agent, skin defense enhancer agent, skin clarifier agent, skin repair agent, slimming agent, smoothing agent, softening agent, soothing agent, sun care agent, sunless tanning agent, tensing agents and whitening agent, or any other agent adapted for use in a cosmetic regimen that comprises topical application of said cosmetic composition, and which complements or supplements the effect of the compound of the present invention.

Without being so limited, agents that modulate cell differentiation or proliferation include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin D and its derivatives (cholecalciferol, ergocalciferol, 25-hydroxycholecalciferol), growth factors and estradiol derivatives.

Without being so limited, anaesthesics include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include lidocaine chlorhydrate and its derivatives.

Without being so limited anti-acne agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include benzoyl peroxide, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), salicylic acid, sulfur, sulfurated lime, alcohol and acetone.

Without being so limited, anti-aging/anti-wrinkle agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include hyaluronic acid, sodium-2-pyrrolidone carboxylate, glycosaminoglycans, kinetin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), epidermal growth factor, ceramide, ethylbisiminomethylguaiacol manganese chloride, glycation inhibitors, *chrysanthellum indicum* extract and aphanizomenon flos aquae extract.

Without being so limited, antibacterial agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include eucalyptus extract, clindamycin phosphate, cavacrol, erythromycin and antibiotics belonging to the group of tetracyclines.

Without being so limited, antifungal agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include econazole, ketoconazole, miconazole, amphotericin B, terbinafine and octopirox.

Without being so limited, anti-inflammatory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, vitamin E and its derivatives (α-tocopherol, δ-tocopherol, γ-tocopherol), chamomile oil, gingko biloba oil and *camellia sinensis* extract.

Without being so limited, anti-irritant/soothing/smoothing/calming agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, *camellia sinensis* extract, lavender oil, aloe vera, linden extract, *epilobium angustifolium* extract, chysanthellum indicum extract, cola nitida extract and alteromonas ferment extract.

Without being so limited, antioxidant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include furfuryladenine, panthenol, lipoic acid, ubiquinone, niacinamide, melatonin, catalase, glutathione, superoxide dismutase, polyphenols, cysteine, allantoin, kinetin, vitamin C and its derivatives (ascorbyl palmitate, magnesuim ascorbyl phosphate, sodium ascorbyl phosphate), vitamin E and its derivatives (α-tocopherol, δ-tocopherol, γ-tocopherol), grape seed extract and *camellia sinensis* extract.

Without being so limited, antipruritic agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include thenaldine, trimeprazine, cyproheptadine.

Without being so limited, anti-rosacea/anti-telangiectasia agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include metronidazole, vasoconstrictors, benzoyl peroxide, azelaic acid, sulphur, soy proteins and glycosaminoglycans.

Without being so limited, anti-seborrhea agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include progesterone derivatives, isoleutrol and hinokitiol.

Without being so limited, sensitive skin agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rose oil and jasmine oil.

Without being so limited, cleansing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include ammonium lauryl sulfate, ammonium laureth sulfate, cocamide MEA, triethanolamine lauryl sulfate, sodium stearate and nettle leaf extract.

Without being so limited, collagen synthesis agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, (β-carotene, retinyl ester), vitamin C and its derivatives (ascorbyl palmitate, magnesium ascorbyl phosphate, sodium ascorbyl phosphate), growth factors and its derivatives.

Without being so limited, exfoliant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include alpha/beta hydroxy acids, salicylic acid, glycolic acid, lactic acid, citrus acid and walnut shell powder.

Without being so limited, facial peeling agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include glycolic acid, lactic acid, trichloroacetic acid and phenol.

Without being so limited, firming/tensing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dimethylaminoethanol, neuro-cosmetic actives (Botox™-like), chitosan, arnica extract, fennel-sweet oil and papaya extract.

Without being so limited, free radical scavenging/antipollution/anti-stress agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include grape seed extract, alpha-tocopherol and the esters thereof, superoxide dismutase, some chelating agents of metals, vitamin C and its derivatives (ascorbyl palmitate, magnesium ascorbyl phosphate, sodium ascorbyl phosphate).

Without being so limited, hair care agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-D-glucosamine, poly-N-acetyl-D-glucosamine, stearalkonium chloride and triethanolamine lauryl sulfate.

Without being so limited, matrix metalloproteinase inhibitory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *camellia sinensis* extract, polyphenols, spatholobi caulis extract, *euonymus alatus* extract, rhizoma notopterygii extract, quercetin, glycosaminoglycans, polymethoxy flavonoid, N-acetyl-cysteine, 2-furildioxime, isoflavone, vitamin C and its derivatives (ascorbyl palmitate, magnesium ascorbyl phosphate, sodium ascorbyl phosphate), retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester) and hydroxamate derivatives.

Without being so limited, moisturizing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include cucumber extract, sodium-2-pyrrolidone carboxylate, sodium PCA, sodium hyaluronate, chitin and its derivatives, alpha hydroxy acids, hyaluronic acid and hydrolysed wheat protein.

Without being so limited, osmoregulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include mannitol, dulcitol and betaine.

Without being so limited, protecting agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-N-acetyl-D-glucosamine, poly-D-glucosamine, alkyloamides, chitosan, *chrysanthellum indicum* extract, *camellia sinensis* extract and alteromonas ferment extract.

Without being so limited, rejuvenating agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rosemary extract, rosewood extract, geranium extract and vitamin E and its derivatives (α-tocopherol, δ-tocopherol, γ-tocopherol).

Without being so limited, skin repair agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), allantoin, eucalyptus extract, lavender oil, rose oil and activators of collagen synthesis and activators of components of the skin's extracellular matrix.

Without being so limited, slimming/anticellulite agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *chrysanthellum indicum* extract, dihydromyricetin, theobromine, theophylline, aminophylline, caffeine, isopropylarterenol hydrochloride, epinephrine, α-MSH agonists, adenylate cyclase activators and phosphodiesterase inhibitors.

Without being so limited, sun care/photo aging agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include PABA (p-aminobenzoic acid) and derivatives, gluconolactone, salicylates, cinnamates, benzophenones, dibenzoylmethanes, oxybenzone, vitamin E and its derivatives (α-tocopherol, δ-tocopherol, γ-tocopherol), ethylbisiminomethylguaiacol manganese chloride, glycosaminoglycans, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), titanium dioxide, octyl methoxycinnamate, benzophenone, octyl salicylate, *epilobium angustifolium* extract, *rumex occidentalis* extract, *chrysanthellum indicum* extract, *camellia sinensis* extract and *alteromonas ferment* extract.

Without being so limited, sunless tanning/melanogenesis stimulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dihydroxyacetone, α-MSH agonists, adenylate cyclase activators and phosphodiesterase inhibitors.

Without being so limited, toning agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include nettle extract, orange blossom extract, rosewood extract and witch hazel extract.

Without being so limited, whitening/pigmentation agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include arbutin, azealeic acid, vitamin C and its derivatives (ascorbyl palmitate, magnesuim ascorbyl phosphate, sodium ascorbyl phosphate), hydroquinone, N-acetyl-4-S-cysteanimylphenol, kojic acid, melanostat (melanostatine), tretinoin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), ruminex occidentalis extract, licorice, mulberry, arctostaphylos uva-ursi (bearberry), tyrosinase inhibitors, melanosome-transfer inhibitors and melanin scavengers.

In an embodiment, the composition of the present invention further comprises a pharmaceutically acceptable topical carrier, vehicle, excipient or additives (i.e. topically/cosmetically acceptable carrier, vehicle, excipient or additives). Such carrier, vehicle, excipient or additives are well known in the art and may be used, for example, to improve final formulation regarding organoleptic properties, skin penetration and accessibility of the active ingredient. Examples of carriers, vehicles or excipients include: buffering agent, carrier agent, chelating agent, conditioner agent, coloring agent, detackifier agent, emollient agent, emulsifier agent, film former agent, foaming agent, humectant agent, lactylate agent, lipophilic agent, lubricant agent, neutralizer agent, oil agent, opacifier agent, preservative agent, solubilizer agent, solvent agent, stabilizer agent, surfactant agent, thickener agent, viscosity agent, water absorbent agent, wetting agent, perfume and thermal water.

The composition of the present invention may be formulated so as to provide for a specifically controlled delivery system. Non-limitative examples of such delivery systems include slow delivery system, rapid delivery system, immediate delivery system, delayed delivery system, zero-order delivery system and dual or multiple speed delivery system. Such controlled delivery systems may be achieved with specific formulations including chemical delivery systems, multiple emulsions, microemulsions, nanoemulsions, encapsulations such as liposomes, microspheres, nanospheres, microsponges, beads and cyclodextrins, polymeric matrices, polymeric cosmetic conjugates, oil body/oleosin, oil-soluble molecular film, skin patches, unit dosages.

Without being so limited, buffering agents are salts of bases/acids, compatible with the nature of the skin and with its pH. Sodium acetate is an example of a frequently used buffer agent.

Without being so limited, carrier agents are ingredients capable of aiding the application of the active ingredient. Isohexadecane is an example of a frequently used carrier.

Without being so limited, chelating agents are ingredients capable of binding mono and divalent cations, such as tetrasodium EDTA and disodium EDTA.

Without being so limited, conditioner agents are ingredients with lubricating action and hydrating effect, such as cetrimonium chloride, dicetyldimonium chloride, trideceth-l2, quaternium-Z7, quaternium-l8, polyquaternium-10, behentrimonium methosulfate, cetearyl alcohol, stearamidopropyl dimethylamine, trimethylsilylamodimethicone, isolaureth-6, octoxynol-4, dimethicone, dimethiconol, cyclopentasiloxane, pareth-7, pareth-9, linoleic acid and glycerin.

Without being so limited, detackifier agents are ingredients capable of adsorbing onto tacky materials and reduce their tendency to adhere, such as cyclopentasiloxane, dimethicone and vinyl dimethicone, phenyl trimethicone, isopropyl esters, isostearate esters, dimethyl sebacate and dipropyl sebacate.

Without being so limited, emollient agents are ingredients with lubricating action and hydrating effect, such as isopropyl palmitate, sunflower seed oil, mineral oil, stearyl stearate, isopropyl myristate, lanolin, caprylic, capric triglyceride, cyclopentasiloxane, dimethicone, vinyl dimethicone, bis-phenylpropyl dimethicone, alkyl dimethicone, sorbitan stearate, sucrose distearate, myristyl alcohol, myristyl lactate, cetyl acetate, dicaprylyl ether, floraester-20, maleated soybean oil, cyclomethicone, shea butter, hydrogenated coconut oil, isopropyl palmitate, diisostearoyl trimethylolpropane siloxy silicate and alkyl benzoate.

Without being so limited, emulsifier agents are ingredients capable of preventing the separation of immiscible substances in an emulsion, of helping to distribute evenly one substance in another, of improving texture, homogeneity, consistency and stability, such as cetearyl alcohol, glyceryl stearate, alkyl acrylate crosspolymer, stearic acid, emulsifying wax, sorbitan oleate, sorbitan stearate, polysorbate, polyethylene glycopolysorbate, triethanolamine, cyclopentasiloxane, dimethicone copolyol, PEG-30 dipolyhydroxystearate, sucrose distearate, PEG-100 stearate, sodium dioctylsulfosuccinate, polyacrylamide, isoparaffin, laureth-7, cetyl phosphate, DEA cetyl phosphate, glycol stearate, stearyl alcohol, cetyl alcohol, behentrimonium methosulfate and ceteareth-2.

Without being so limited, film former agents are ingredients capable of forming a dimensionally stable and continuous film to minimize the formula tackiness, such as wheat protein, eicosene copolymer, perfluoromethylisopropyl ether, diisostearoyl trimethylolpropane siloxy silicate, trimethylsiloxysilicate, dimethicone, vinyl dimethicone and cyclopentasiloxane.

Without being so limited, foaming agents are ingredients capable of regulating the amount of air in a product, such as lauramide DEA and cocamide MEA, disodium laureth sulfosuccinate, disodium N-octadecyl sulfosuccinamate, ammonium lauryl sulphate, triethanolamine lauryl sulfate, sodium lauryl sulphate and sodium 2-ethylhexylsulfate.

Without being so limited, humectant agents are ingredients capable of maintaining constant humidity and retaining moisture, such as glycerine, PEG-8, butylene glycol and propylene glycol.

Without being so limited, lubricant agents are ingredients capable of adding slipperiness and reducing friction to improve application, such as dimethicone and dimethicone copolyol.

Without being so limited, neutralizer agents are ingredients capable of changing the acid-alkaline balance, such as triethanolamine and sodium hydroxide.

Without being so limited, opacifier agents are ingredients capable of changing the look of a clear or translucent product to a creamier or pearlier one, such as glyceryl stearate and PEG-100 stearate.

Without being so limited, preservative agents are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben.

Without being so limited, solubilizer agents are ingredients capable of allowing incompatible ingredients to become part of a homogeneous solution, such as polysorbate, ceteareth, steareth and PEG.

Without being so limited, stabilizer agents are ingredients capable of maintaining physical and chemical properties during and after processing, preventing or limiting changes in the physical properties of a substance during product life, such as polyethylene, sodium chloride, stearyl alcohol, xanthan gum, tetrasodium EDTA and dimethicone copolyol.

Without being so limited, surfactant agents are ingredients capable of reducing surface tension when dissolved in water or a water solution, reducing interfacial tension between two liquids or between a liquid and a solid, such as sodium dioctylsulfosuccinate, octoxynol-40, isolaureth-6, ammonium lauryl sulfate, lauryl alcohol, lauramide DEA and cocoamidopropyl betaine.

Without being so limited, thickener agents are ingredients capable of absorbing water to impart body, improve the consistency or texture, and stabilize an emulsion, such as stearic acid, magnesium aluminum silicate, carbomer, alkyl acrylate crosspolymer, polyacrylamide, isoparaffin, laureth-7, cetyl alcohol, xanthan gum, alkyl dimethicone, hydroxyethylcellulose, glyceryl stearate, pentaerythrityl tetrastearate, stearyl alcohol and polyquaternium-10.

Without being so limited, viscosity agents are ingredients capable of controlling the degree of fluidity and the internal resistance to flow exhibited by a fluid, such as magnesium aluminum silicate, caprylyl glycol and myristyl alcohol.

Without being so limited, water absorbent agents are ingredients capable of absorbing the product's water to maintain the moisture, such as carboxyvinyl polymer, acrylic copolymer, polyacrylamide, polysaccharides, natural gum, clay, modified clay, metallic salt and fatty acid.

Without being so limited, wetting agents are ingredients capable of reducing the surface tension of the water for better penetration or spread over the surface, such as caprylate, caprylyl glycol, glyceryl caprate, polyglyceryl-2 caprate, polyglyceryl-6, polyglyceryl-3 laurate and TEA-laureth sulfate.

The compound or composition of the present invention may be packaged in any suitable manner, including but not limited to, a jar, a bottle, a tube, a stick, a roller-ball applicator, an aerosol spray device, etc., in the conventional manner. The compound or composition of the present invention could be packaged as a kit of two or more separate compartments, including one containing the active ingredients and a second containing a topically/dermatologically-acceptable vehicle, which may be mixed together at some fixed time point prior to application. For example, the active ingredients, in the form of a cream, a powder, a tablet, a capsule or a liquid, may be contained in sealed, single-use packets, which may be opened and mixed with the topically-acceptable vehicle, which may also be stored in pre-measured form in sealed, single-use packets. Alternatively, the active ingredients and the topically-acceptable vehicle may be provided in larger quantities from which the needed amount could be withdrawn using various measuring devices, such as a measuring spoon or cup for solids, or a calibrated vial or dropper for liquids. The compound or composition of the present invention may be spread onto a substrate and then subsequently packaged. Suitable substrates include dressings, including film dressings, and bandages. In an embodiment, the kit or package may comprise instructions for use/application, e.g., instructions for preventing, reducing, delaying or treating a skin condition.

In another aspect, the present invention provides the use (e.g., cosmetic or therapeutic use) of a compound of formula (I) for preventing, reducing, delaying or treating a skin condition in a subject.

In another aspect, the present invention relates to the use of a compound of formula (I) for improving the consistency and thickness of the dermis by ameliorating the dermis homogeneity.

In another aspect, the present invention relates to the use (e.g., cosmetic use) of a compound of formula (I) for inducing and/or increasing the production of a DEJ molecule in a biological system. In a further embodiment, the above-mentioned DEJ molecule is laminin-5 and/or collagen VII.

In another aspect, the present invention relates to the use of a compound of formula (I) for reinforcing the dermo-epidermal junction (DEJ).

In another aspect, the present invention provides the use of a compound of formula (I) for the preparation of a medicament for preventing, reducing or treating a skin condition.

In another aspect, the present invention provides the use of a compound of formula (I) for the preparation of a medicament for improving the consistency and thickness of the dermis by ameliorating the dermis homogeneity.

In another aspect, the present invention relates to the use of a compound of formula (I) for the preparation of a medicament for inducing and/or increasing the production of at least one DEJ molecule in a biological system. In an embodiment, the above-mentioned at least one DEJ molecule is laminin-5 and collagen VII.

In another aspect, the present invention relates to the use of a compound of formula (I) for the preparation of a medicament for reinforcing the dermo-epidermal junction (DEJ).

In an embodiment, the above-mentioned skin condition is an aging-related skin condition (e.g., intrinsic aging) of the skin. The aging-related skin condition may, for example, involve wrinkles, fine lines, age spots, sun damage (particularly UV radiation-induced oxidative stress), blemishes, hyperpigmented skin, age spots, increased skin thickness, loss of skin elasticity and collagen content, dry skin, lentigines, and/or melasmas or any combination thereof. In an embodiment, the above-mentioned aging-related skin condition is the appearance or presence of (a) wrinkles, (b) fine lines or (c) both (a) and (b), on the skin.

In another embodiment, the above-mentioned skin condition is skin damage caused by a cosmetic or therapeutic treatment or by an injury (e.g., a surgical intervention involving the skin, laser treatment of the skin, dermabrasion or peeling (e.g., to assist in the healing process)).

In an embodiment, the above-mentioned biological system is a cell or cells, a tissue, an organ or a subject. In a further embodiment, the above-mentioned cell or cells is/are a skin cells such as a fibroblast, or a combination of cells including fibroblasts. In another embodiment, the above-mentioned organ is skin.

The method of delivery of the compound or composition of the present invention may vary, but usually involves application to an area of skin prone to, or affected by, an aging-related skin condition, e.g., any skin condition or disorder associated with, caused by, or affected by, intrinsic aging and/or extrinsic aging. The aging-related skin condition may, for example, involve wrinkles, fine lines, age spots, sun damage (e.g., UV radiation-induced oxidative stress), blemishes, hyperpigmented skin, increased skin thickness, loss of skin elasticity and collagen content, dry skin, lentigines, and/or melasmas.

A cream, lotion, gel, ointment, paste or the like may be spread on the affected surface and gently rubbed in. A solution may be applied in the same way, but more typically will be applied with a dropper, swab, or the like, and carefully applied to the affected areas.

The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once or twice daily.

In an embodiment, the above-mentioned subject is a mammal. In a further embodiment, the above-mentioned mammal is a human.

The present invention is illustrated in further details by the following non-limiting examples.

EXAMPLE 1

Synthesis of $CH_3$—$(CH_2)_4$—CO-Lys-Gly-His-Lys-$NH_2$ (peptide I, SEQ ID NO: 1)

Peptide I was synthesized on a solid support with a Rink amide resin whose functionalization is between 0.3 and 0.6 mmole/g of resin. The Rink amid resin was first prepared by washing with Dimethylformamide (DMF) (2 washings), then followed by the deprotection step described below. For each amino acid to be coupled, the following steps were repeated: coupling the amino acid, washing the resin, deprotecting the main chain's amino function, and then washing the resin again. The four amino acid residues comprised in the resulting peptide were in the L configuration.

Coupling: two benzotriazole-1-yl-oxy-tris-(dimethylamino)-phosphonium hexafluorophosphate (BOP) (or 2-(1H-benzotriazol-1-yl) 1,1,3,3-tetramethyluronium hexafluorophosphate, HBTU) equivalents, two diispropylethylamine (DIEA) (or N-methylmorpholine, NMM) equivalents and two 9-fluorenylméthoxycarbonyl (Fmoc)-AA-OH equivalents, for 2 hours in DMF.

Washing: two DMF washings, one methanol washing, two dichloromethane washings and one DMF washing.

Deprotection: an 80/20 DMF/piperidine mix with 2% ethanediol (to trap radicals), once for 3 minutes and then for 7 minutes.

Washing: (same as above).

After the amino acids have been coupled, the acid was coupled on the N-terminal function in the same manner as an amino acid and the peptide was cleaved from the resin using a 50/50 Trifluoroacetic acid (TFA)/dichloromethane mix with 2% ethanediol for 90 minutes.

Dichloromethane and TFA were evaporated under a nitrogen flow, followed by precipitation with diethylether and purification by preparative liquid chromatography with a reversed-phase C18 column.

$CH_3$—$(CH_2)_4$—CO-Lys-Gly-His-Lys-$NH_2$ (peptide I) was synthesized using the following protected amino acids: Fmoc-His(Trt)-OH, Fmoc-Lys(Boc)-OH, and Fmoc-Gly-OH and coupled on the N-terminal function with an hexanoic acid.

EXAMPLE 2

Synthesis of $CH_3$—$(CH_2)_6$—CO-Lys-Gly-His-Lys-$NH_2$ (peptide II; SEQ ID NO: 2)

Peptide II was synthesized using the same procedure as that described in Example 1, except that an octanoic acid, instead of an hexanoic acid, was used for coupling onto the N-terminal function of the first lysine residue. The four amino acid residues comprised in the resulting peptide were in the L configuration.

EXAMPLE 3

Synthesis of $CH_3$—$(CH_2)_2$—CO-Lys-Gly-His-Lys-$NH_2$ (peptide III; SEQ ID NO: 3)

Peptide III was synthesized using the same procedure as that described in Example 1, except that a butanoic acid, instead of an hexanoic acid, was used for coupling onto the N-terminal function of the first lysine residue. The four amino acid residues comprised in the resulting peptide were in the L configuration.

EXAMPLE 4

Synthesis of $CH_3$—$(CH_2)_8$—CO-Lys-Gly-His-Lys-$NH_2$ (peptide IV; SEQ ID NO: 4)

Peptide IV was synthesized using the same procedure as that described in Example 1, except that a decanoic acid, instead of an hexanoic acid, was used for coupling onto the N-terminal function of the first lysine residue. The four amino acid residues comprised in the resulting peptide were in the L configuration.

EXAMPLE 5

Effect of Peptide I on the Neosynthesis of Laminin in a Model of Normal Human Fibroblasts Normal human dermal fibroblasts were incubated for 48 hours in absence or presence of Transforming Growth Factor (TGF)-β at 50 ng/ml or of peptide I at two concentrations, namely $10^{-6}$M and $10^{-7}$M. At the end of the incubation period, laminins were quantified with the E.I.A. Enzyme Immuno Assay kit. Proteins contained in the cell lysate were also quantified by spectrocolorimetry according to the Bradford method. TGF-β and peptide I were tested in dose-response on the fibroblasts.

The data presented in Table I below represent the relative increase in laminin synthesis in a human dermal fibroblast culture medium in monolayers in the presence of peptide I, or TGF-β, as compared to untreated cells (control).

TABLE I

| Laminins (ng/μg proteins) | % increase |
|---|---|
| Control | 100.0% |
| TGF-β (50 ng/ml) | 109.9% |
| Peptide I ($10^{-6}$M) | 125.8% |
| Peptide I ($10^{-7}$M) | 125.9% |

These results indicate that peptide I increases laminin synthesis in human dermal fibroblast cells.

EXAMPLE 6

Effect of Peptide I on the Synthesis of Collagen VII in a Human Skin Model

Fragments of normal human skin were treated or not in the presence of a dermal corticosteroid at 0.05% w/v and peptide I at a concentration of $10^{-7}$M. Dermal corticosteroid are known to alter cell metabolism. The skin samples were then frozen at day 3 for an immunohistochemical analysis of collagen VII. The immunodetection was performed with a 3 coats indirect immunoperoxidase method (ABC Peroxidase kit, Vector laboratories) using a primary antibody specific to collagen VII.

Quantification of collagen VII labelling was determined using the semi-quantitative scores presented in Table II:

TABLE II

| | |
|---|---|
| No labeling of collagen VII | Score 0 |
| Light labeling of collagen VII | Score 1 |
| Moderate labeling of collagen VII (normal skin) | Score 2 |
| Normal labeling of collagen VII (normal skin) | Score 3 |
| Overexpression of collagen VII | Score 4 |

The results presented in Table III indicate that peptide I increases the synthesis of collagen VII in a human skin model.

TABLE III

| Treatment | Score | Relative change |
|---|---|---|
| Control skin (no treatment) | 1.9 ± 0.8 | — |
| Skin + corticosteroids | 1.6 ± 0.5 | −16% |
| Skin + corticosteroids + peptide I $10^{-7}$M | 2.25 ± 0.2 | +34% |

EXAMPLE 7

Effect of Peptide I on the Synthesis of Laminin-5 in a Model of Human Skin

Fragments of normal human skin were treated or not in the presence of a dermal corticosteroid at 0.05% w/v or peptide I at a concentration of $10^{-7}$M. The skin samples were then frozen at day 3 for an immunohistochemical analysis of laminin-5. The immunodetection was performed with a 3 coats indirect immunoperoxidase method (BC Peroxidase kit, Vector laboratories) using a primary antibody specific to laminin-5.

Quantification of laminin-5 labelling was determined using the semi-quantitative scores presented in Table IV:

TABLE IV

| | |
|---|---|
| No labeling of laminin 5 | Score 0 |
| Light labeling of laminin 5 | Score 1 |
| Moderate labeling of laminin 5 (normal skin) | Score 2 |
| Normal labeling of laminin 5 (normal skin) | Score 3 |
| Overexpression of laminin 5 | Score 4 |

The results presented in Table V indicate that peptide I increases the synthesis of laminin-5 in a human skin model.

TABLE V

| Treatment | Score | Relative change |
|---|---|---|
| Control skin (no treatment) | 2.1 ± 1.3 | — |
| Skin + corticosteroids | 1.17 ± 0.8 | −45% |
| Skin + corticosteroids + peptide I $10^{-7}$M | 2.2 ± 0.8 | +49% |

EXAMPLE 8

In vivo Anti-Wrinkle Activity of Peptide I

Peptide I was tested in the formulation described in Table VI below versus its placebo on 30 subjects (+10%) selected according to the inclusion/non inclusion criteria.

TABLE VI

Anti-wrinkle aqueous gel comprising peptide I

| Constituent | Amount |
|---|---|
| Water | 69.66 (w/w) |
| Caprylic/Capric Triglyceride | 10% (w/w) |
| Myristyl Myristate | 4.5% (w/w) |
| Glycerin | 3% (w/w) |
| Butylene Glycol | 3% (w/w) |
| Glyceryl Stearate | 3% (w/w) |
| Polysorbate 60 | 3% (w/w) |
| *Butyrospermum Parkii* (Shea butter) fruit | 1.5% (w/w) |
| Phenoxyethanol, methylparaben, ethylparaben, butylparaben, propylparaben, Isobutylparaben | 0.8% (w/w) |
| Sorbitan Stearate | 0.75% (w/w) |
| Dimethicone | 0.60% (w/w) |
| Tea-Carbomer | 0.16% (w/w) |
| Peptide 1 | 5 ppm |

Peptide I was tested at 5 ppm ($0.88 \times 10^{-5}$M).

The study lasted 56 days following the first application. Volunteers applied the product twice daily on a randomised crow's foot of the temple.

The study was a simple blind test, comparing the results obtained at one treated area following application of the composition comprising peptide I with those obtained at another treated area with the placebo.

The evaluation of the efficacy of the formulation comprising peptide I was performed using: (a) illustrative digital photographs of the crow's feet; and (b) Silicone rubber replicas of the crow's feet (analysis of the wrinkles and of the skin network by fringe projection).

Photographs of the cow's feet of one of the volunteers at day 0 and day 28 after application of the formulation comprising peptide I are presented in FIG. 1.

Figure 2:
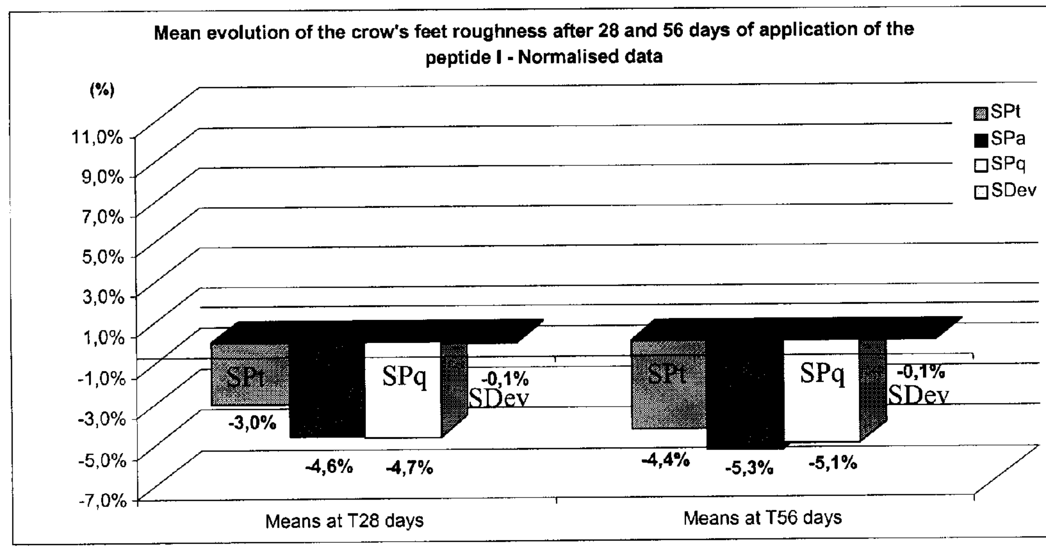
FIG. 2 is a graph showing the mean evolution of the crow's feet roughness after 28 and 56 days of application of a composition comprising peptide I.

In vitro fringe projection—Topometry—Wrinkles. The relief of the skin was reproduced (in vitro) via a silicone rubber replica. All the silicone rubber replicas were analysed by fringe projection to observe the cutaneous relief. The following parameters were measured: (a) SPa: Average roughness; (b) SPq: Average dispersal of the variations of the relief; (c) SPt: Maximum amplitude of the relief and (d) SDev: Developed Surface. The results of these experiments are presented in FIG. 2.

Figure 3:
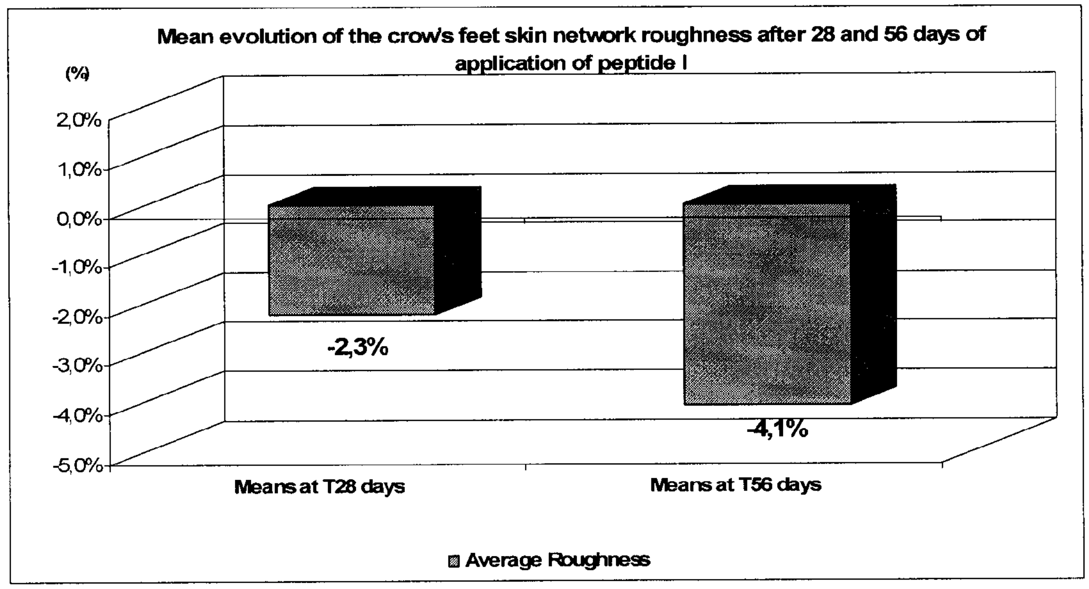
FIG. 3 is a graph showing the mean evolution of the crow's feet skin network roughness after 28 and 56 days of application of a composition comprising peptide I.

In vitro fringe projection—Analysis of the skin network. All the replicas were analysed by fringe projection to observe the skin network analysis. The following parameters were measured: (a) SRa: Average roughness (mm); and (b) SRq: Average with regards to the average quadratic (mm). The results of these experiments are presented in FIG. 3.

These data show a potent efficacy of peptide I for the reduction of the wrinkles after 28 and 56 days application as well as a reduction of the crow's feet skin network roughness.

EXAMPLE 9

Long Term in vivo Anti Ageing Activity of Peptide I

Peptide I was tested in the formulation described in Table VI above versus its placebo on 27 subjects, selected according to the inclusion/non inclusion criteria.

Peptide I was tested at 5 ppm ($0.88 \times 10^{-5}$M). The study was a simple blind test, comparing the results obtained at one area following application of the composition comprising peptide I with those obtained at another area following application of the composition comprising the placebo.

Peptide I or placebo were applied during 168 days (6 months) on the crow's foot and the texture of the dermis was analysed at day 0 and day 168 by high resolution ultrasound (20 MHz). The texture analysis used a technique of second order statistic: co-occurrence matrices method. Two co-occurrence parameters were calculated: entropy of co-occurrence matrix and homogeneity. Entropy corresponds to a human visual perception of coarseness. Homogeneity corresponds to the texture homogeneity.

Table VII summarises the average percentage of variation (T 168 days-T0)/T0 of the studied parameters calculated from the average values.

TABLE VII

Texture of dermis on the temple

| Texture of the dermis on the temple | Variaton % | Placebo | Peptide I |
|---|---|---|---|
| The co-occurrence entropy | (T 168 days − T0)/T0 | 0.0% | +1.3% |
| The co-occurrence homogeneity | (T 168 days − T0)/T0 | +1.8% | +2.1% |

The statistical analysis of the results obtained with the Peptide I treatment, showed significant increase of the two studied parameters:

Co-occurrence entropy: +1.3% ($p=3.00\times10^{-3}$, Wilcoxon test, two tailed, for paired groups, 5%).

Co-occurrence homogeneity: +2.1% ($p=3.60\times10^{-2}$, Wilcoxon test, two tailed, for paired groups, 5%).

Figure 4:
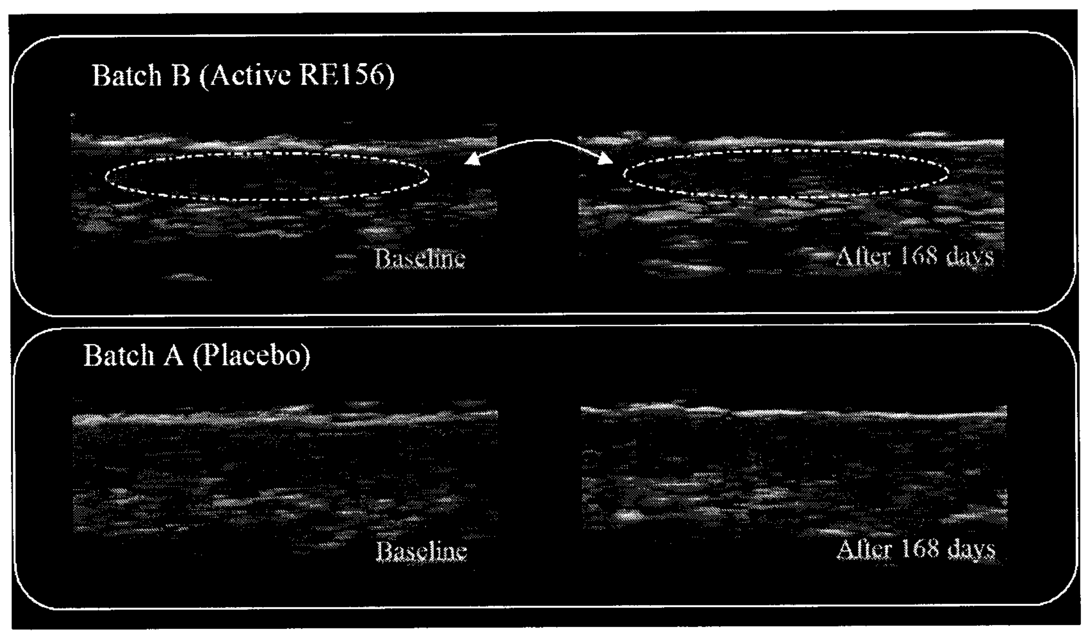
FIG. 4 is a high resolution ultrasound image (20 MHz) of the texture of the dermis at day 0 and day 168 after application of a composition comprising peptide I or a placebo.

The analysis of the dermis on the basis of the ultrasound image is shown in FIG. 4.

EXAMPLE 10

An Anti-Wrinkle Oil/Water Emulsion Comprising Peptide I

| Constituent | Amount |
|---|---|
| Oil phase | |
| Cetearyl alcohol (and) Cetearyl glucoside (Montanov ® 68) | 5% (w/v) |
| Jojoba oil | 5% (w/v) |
| Vaseline oil | 5% (w/v) |
| Isopropyl palmitate | 7% (w/v) |
| Aqueous phase | |
| Glycerine | 5% (w/v) |
| Polyacrylamide and C13-14 Isoparaffin and Laureth-7 (Sepigel ® 305) | 0.3% (w/v) |
| Phenoxyethanol, methylparaben, butylparaben, ethylparaben, propylparaben (Phenonip ®) | 0.5% (w/v) |
| Perfume | 0.2% (w/v) |
| Peptide 1 | 10 ppm |
| Water qsf | 100% |

Although the present invention has been described hereinabove by way of specific embodiments thereof, it can be modified, without departing from the spirit and nature of the subject invention as defined in the appended claims.

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal group is modified with a
      CH3-CH2-CH2-CH2-CH2-CO group
<220> FEATURE:
<221> NAME/KEY: MOD_RES
<222> LOCATION: (4)..(4)
<223> OTHER INFORMATION: AMIDATION

<400> SEQUENCE: 1

Lys Gly His Lys
1


<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal group is modified with a
      CH3-CH2-CH2-CH2-CH2-CH2-CH2-CO group
<220> FEATURE:
<221> NAME/KEY: MOD_RES
<222> LOCATION: (4)..(4)
<223> OTHER INFORMATION: AMIDATION

<400> SEQUENCE: 2

Lys Gly His Lys
1


<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal group is modified with a
      CH3-CH2-CH2-CO group
<220> FEATURE:
<221> NAME/KEY: MOD_RES
<222> LOCATION: (4)..(4)
<223> OTHER INFORMATION: AMIDATION

<400> SEQUENCE: 3

Lys Gly His Lys
1


<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: The amino terminal group is modified by a
```

-continued

```
      CH3-CH2-CH2-CH2-CH2-CH2-CH2-CH2-CH2-CO group
<220> FEATURE:
<221> NAME/KEY: MOD_RES
<222> LOCATION: (4)..(4)
<223> OTHER INFORMATION: AMIDATION

<400> SEQUENCE: 4

Lys Gly His Lys
1


<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is L-lys or D-lys, or a L- or D-lys residue
      in which the NH2 group of the side chain comprises a modification
      selected from a replacement with a hydrogen (deamination), an
      acetylation, a benzoylation, and a palmitoylation
<220> FEATURE:
<221> NAME/KEY: MISC_FEATURE
<222> LOCATION: (1)..(1)
<223> OTHER INFORMATION: The amino terminal is modified with a
      CH3-(CH2)n-CO- group, wherein n = 2, 3, 4, 5, 6, 7 or 8
<220> FEATURE:
<221> NAME/KEY: MISC_FEATURE
<222> LOCATION: (3)..(3)
<223> OTHER INFORMATION: Xaa at position 3 is L-histidine or D-histidine
<220> FEATURE:
<221> NAME/KEY: MISC_FEATURE
<222> LOCATION: (4)..(4)
<223> OTHER INFORMATION: Xaa is L-lys or D-lys, or a L- or D-lys residue
      in which the NH2 group of the side chain comprises a modification
      selected from a replacement with a hydrogen (deamination), an
      acetylation, a benzoylation, and a palmitoylation
<220> FEATURE:
<221> NAME/KEY: MISC_FEATURE
<222> LOCATION: (4)..(4)
<223> OTHER INFORMATION: The carboxy terminal is modified with a
      N(Z)(Z') group, wherein Z and Z' are independently of each other a
      hydrogen, a methyl group, an ethyl group, a phenyl group, an hexyl
      group, a decyl group or an hexadecyl group
<220> FEATURE:
<221> NAME/KEY: MISC_FEATURE
<222> LOCATION: (4)..(4)
<223> OTHER INFORMATION: N(Z)(Z') group wherein Z and Z' are
      independently of each other a hydrogen, a methyl group, an ethyl
      group, a phenyl group, a hexyl group, a decyl group or a hexadecyl
      group

<400> SEQUENCE: 5

Xaa Gly Xaa Xaa
1
```

The invention claimed is:

1. A compound of the formula:

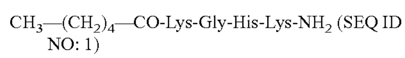

$CH_3$—$(CH_2)_4$—CO-Lys-Gly-His-Lys-$NH_2$ (SEQ ID NO: 1)

wherein:

each Lys is independently of the other a L- or D-lysine residue;

His is a L- or D-histidine residue;

or a racemate, an enantiomer or a diastereomer thereof, or mixtures thereof, or a salt thereof.

2. The compound of claim 1, wherein the lysine and histidine residues are in L-configuration.

3. A composition comprising the compound according to claim 1, and a topically, cosmetically or pharmaceutically acceptable excipient or carrier.

4. The composition of claim 3, wherein said composition comprises between about $10^{-8}$ M and about $10^{-2}$ M of said compound.

5. The composition of claim 4, wherein said composition comprises between about $10^{-6}$ M and about $10^{-5}$ M of said compound.

6. The composition of claim 3, wherein said composition is a topical composition.

7. The composition of claim 3, wherein said composition is an aqueous solution, a cream, a water-in-oil emulsion, a oil-in-water emulsion, a gel, a spray, an ointment, a lotion, or a paste.

8. The composition of claim 3, further comprising at least one additional active agent.

9. A method of preventing, reducing, delaying or treating the appearance or presence of (a) wrinkles, (b) fine lines or (c) both (a) and (b), on the skin in a subject, said method comprising administering an effective amount of the compound of claim 1, to said subject.

10. The method of claim 9, wherein the administration is topical.

11. The method of claim 9, wherein said effective amount is between about $10^{-8}$M and about $10^{-2}$M of said compound.

12. The method of claim 11, wherein said effective amount is between about $10^{-6}$M and about $10^{-5}$M of said compound.

13. A method for inducing or increasing the production of at least one dermo-epidermal junction (DEJ) molecule in a biological system, said method comprising contacting said biological system with the compound of claim 1, or the composition of claim 8.

14. The method of claim 13, wherein said at least one DEJ molecule is (a) laminin-5, (b) collagen VII, or (c) both (a) and (b).

15. The method of claim 13, wherein said biological system is a cell, a tissue or an organ.

16. The method of claim 15, wherein said cell is a skin cell.

17. The method of claim 15, wherein said organ is skin.

18. A kit or package comprising the compound of claim 1, together with (i) instructions for preventing, reducing, delaying or treating the appearance or presence of (a) wrinkles, (b) fine lines or (c) both (a) and (b), on the skin in a subject; and/or together with (ii) a container.

19. A kit or package comprising the composition of claim 3, together with (i) instructions for preventing, reducing, delaying or treating the appearance or presence of (a) wrinkles, (b) fine lines or (c) both (a) and (b), on the skin in a subject; and/or together with (ii) a container.

* * * * *